(12) United States Patent
Hawkins

(10) Patent No.: US 6,194,394 B1
(45) Date of Patent: Feb. 27, 2001

(54) COAGULATION CONTROLS FOR PROTHROMBIN TIME (PT) AND ACTIVATED PARTIAL THROMBOPLASTIN TIME (APTT) ASSAYS

(75) Inventor: Pamela L. Hawkins, Ballwin, MO (US)

(73) Assignee: Sigma-Aldrich Co., Highland, IL (US)

( * ) Notice: Subject to any disclaimer, the term of this patent is extended or adjusted under 35 U.S.C. 154(b) by 0 days.

(21) Appl. No.: 09/108,732

(22) Filed: Jul. 1, 1998

(51) Int. Cl.[7] .................. A61K 31/727; C08B 37/10; C12Q 1/56
(52) U.S. Cl. ..................... 514/56; 536/21; 435/13
(58) Field of Search ................. 514/56; 536/21; 435/13

(56) References Cited

U.S. PATENT DOCUMENTS

| | | | |
|---|---|---|---|
| 4,948,724 | * 8/1990 | Yin | 435/13 |
| 5,169,786 | * 12/1992 | Carroll et al. | 436/69 |
| 5,221,614 | * 6/1993 | Enomoto | 435/13 |
| 5,308,755 | * 5/1994 | Nesheim et al. | 435/7.4 |
| 5,702,912 | * 12/1997 | Hemker et al. | 435/13 |

OTHER PUBLICATIONS

Soloway et al. *Amer. J. Clin. Pathol*, 1973, 59(4), 587–90.*
Fischer et al. *Clin. Chem.* 1989, 35(3), 483–486.*

* cited by examiner

*Primary Examiner*—Kathleen K. Fonda
(74) *Attorney, Agent, or Firm*—Senniger, Powers, Leavitt & Roedel

(57) ABSTRACT

Coagulation control compositions suitable for use in connection with PT and/or APTT assays are disclosed along with their methods of preparation and methods of use. Preferred coagulation controls comprise plasma and an anticoagulant having activity for enhancing the activity of antithrombin III (ATIII) or of heparin co-factor II (HCII) against thrombin or against a clotting factor selected from the group consisting of factors IXa, Xa and XIa. The anticoagulant is preferably a glycosaminoglycan such as heparin, a heparin derivative or a heparin analog. The anticoagulant is preferably combined with (1) an abnormal plasma (e.g. activated plasma or factor-deficient plasma) and/or (2) a primate plasma (e.g. human plasma), and a non-primate mammalian plasma (e.g. bovine plasma). In the latter case, the non-primate mammalian plasma is preferably present in the coagulation control composition in an amount of not more than about 12% by volume, relative to total volume.

71 Claims, 2 Drawing Sheets

COAGULATION CONTROLS FOR PROTHROMBIN TIME (PT) AND ACTIVATED PARTIAL THROMBOPLASTIN TIME (APTT) ASSAYS

BACKGROUND OF THE INVENTION

The present invention generally relates to diagnostic coagulation assays, and specifically, to control samples suitable for use in connection therewith. The invention particularly relates to coagulation controls suitable for both prothrombin time and activated partial thromboplastin time assays.

Coagulation control materials are used in the clinical laboratory for quality control of the prothrombin time (PT) and activated partial thromboplastin time (APTT) assays. PT assays employ thromboplastin reagents and have been used extensively for evaluating blood coagulation associated with the extrinsic pathway. APTT assays employ an intrinsic pathway activator, such as micronized silica, and a phospholipid component of a thromboplastin reagent (without tissue factor protein) for evaluating coagulation associated with the intrinsic pathway. Both PT and APTT assays are used clinically for screening patients' plasma for coagulation factor deficiencies. Clinical screenings are employed, for example, during routine checkups and prior to surgery. PT and APTT assays are also used for monitoring treatment with anticoagulants. For example, PT assays are routinely employed to monitor oral anti-coagulant treatment with coumarin (Warfarin™, Coumadin™), and APTT assays are typically used for monitoring anticoagulant treatment with heparin.

Coagulation controls are used for quality control evaluations of the PT and APTT assay systems. The controls are essential in view of potential variation in reagents employed in these assays, potential inaccuracies in the devices used to measure clotting time, and potential effects of inaccurate anticoagulant dosage. Commercial coagulation controls have been designed to mimic three physiologic conditions: (1) "Control Level I" controls mimic normal coagulation and are intended to be representative of an individual without coagulation deficiencies; (2) "Control Level II" controls are intended to mimic the coagulation of an individual undergoing mild anticoagulant therapy; and (3) "Control Level III" controls are intended to mimic the coagulation of an individual undergoing relatively high anticoagulant therapy.

Various types of coagulation controls are known in the art. Typically, coagulation controls are designed to be suitable for use with (1) both the PT and APTT assays, (2) the PT assay only or (3) the APTT assay only. The controls designed exclusively for use in evaluating only the APTT assay are referred to in the art as heparin controls. While effective for APTT assays, such controls are ineffective for use in evaluating PT assay systems. The present invention is directed to general coagulation controls that can be employed for evaluating both PT and APTT assay systems.

A primary performance criteria for a coagulation control is its stability over time. Zucker et al. reported that coagulation controls prepared by buffering plasma specimens with N-2-hydroxyethylpiperazine-N'-2-ethanesulfonic acid (HEPES) and lyophilizing provided stability in the reconstituted control for eight hours at 25° C. Zucker et al., *Preparation of Quality Control Specimens for Coagulation*, Am. J. Clin. Path. 53:924–927 (1970). Brozovic and co-workers prepared controls from plasma samples of patients on oral anti-coagulant therapy in combination with HEPES, trisodium citrate and aprotinin, and reported stability of 4 hours to 6 hours after reconstitution when stored at 4° C. Brozovic et al., *Stability of Freeze-Dried Plasma Prepared from Patients on Oral Anticoagulants*, J. Clin. Path., 26:857–863 (1973). U.S. Pat. No. 5,721,140 to Speck et al. discloses a coagulation control comprising normal human plasma, clotting factor-deficient non-primate mammalian plasma and aprotinin, and report that the controls are stable in the absence of a buffer for up to five days. Numerous other patents and literature references describe various coagulation controls. Exemplary patents include U.S. Pat. No. 3,947,378 to Babson, U.S. Pat. No. 4,007,008 to Becker et al., U.S. Pat. No. 4,056,484 to Heimburger et al. and U.S. Pat. No. 4,127,502 to Li Mutti et al.

While many variations in coagulation control compositions have been reported in the art, such controls remain limited with respect to stability—particularly once reconstituted from the lyophilized form in which they are typically sold. Reconstituted commercially-available coagulation controls stored for more than about eight hours do not provide consistent, reproducible clotting times as determined by PT and/or APTT assays. Moreover, precipitates and fibrin have been observed in such reconstituted controls. There remains a need, therefore, for coagulation controls suitable for use in connection with PT and APTT assays that have enhanced stability.

SUMMARY OF THE INVENTION

It is therefore an object of the present invention to prepare coagulation controls having enhanced stability over time—as demonstrated by consistent clotting times in PT and APTT assays and by the absence of formation of particulate and/or fibrin matter. It is also an object of the invention to be able to produce such controls, on a commercial scale, using readily available starting materials, conventional processing equipment, and existing U.S. Food and Drug Administration (FDA) good manufacturing practices (GMP).

Briefly, therefore, the present invention is directed to coagulation controls suitable for use in connection with both prothrombin time (PT) and activated partial thromboplastin time (APTT) assays. The coagulation control comprises plasma and an anticoagulant having activity for enhancing the activity of antithrombin III (ATIII) and/or of heparin co-factor II (HCII) against thrombin and/or against blood clotting factors such as factors IXa, Xa and/or XIa. The plasma preferably includes primate plasma and a non-primate mammalian plasma. The anticoagulant is preferably a glycosaminoglycan such as heparin.

The invention is directed, moreover, to a coagulation control comprising primate plasma, non-primate mammalian plasma, and an anticoagulant such as a glycosaminoglycan having activity as described above, with the concentration of anticoagulant ranging from about 0.01 U/ml to about 0.15 U/ml, and preferably from about 0.01 U/ml to about 0.1 U/ml, where U is heparin-equivalent units. The human plasma can be normal human plasma or an abnormal human plasma such as an activated plasma or a factor-deficient plasma. The non-primate mammalian plasma is preferably bovine plasma. The glycosaminoglycan is preferably heparin, a heparin derivative, or a heparin analog. A preferred Level I coagulation control comprises normal human plasma, bovine plasma, heparin or a heparin derivative and, optionally, activated plasma, and has a prothrombin time ranging from about 11 seconds to about 13 seconds. A preferred Level II coagulation control comprises factor-deficient human plasma, normal human plasma, bovine plasma, and heparin or a heparin derivative, and has a prothrombin time ranging from about 17 seconds to about 22 seconds. A preferred Level III coagulation control comprises factor-deficient human plasma, normal human plasma, bovine plasma, and heparin or a heparin derivative, and has a prothrombin time ranging from about 25 seconds to about 33 seconds. Each of the aforementioned prothrombin times are determined using a thromboplastin reagent having an International Sensitivity Index (ISI) value of about 2.

The invention is also directed to a coagulation control, typically in lyophilized form, that is suitable upon reconstitution for use in connection with prothrombin time (PT) and activated partial thromboplastin time (APTT) assays. The lyophilized coagulation control comprises primate plasma, non-primate mammalian plasma, and an anticoagulant such as a glycosaminoglycan having activity as described above and present in the composition at a concentration ranging from about 0.1 U/g to about 1.8 U/g, on a dry-weight basis, where U is heparin-equivalent units.

The invention is directed, furthermore, to a coagulation control comprising human plasma and non-primate mammalian plasma, with the ratio of non-primate mammalian plasma to human plasma ranging from about 1:200 to about 1:5, and preferably from about 1:50 to about 1:20. When the coagulation control is a solution, the amount of non-primate mammalian plasma in the solution preferably ranges from about 0.5% to about 12%, by volume.

The invention is directed as well to methods for preparing such coagulation controls. According to one method, primate plasma, non-primate mammalian plasma and an anticoagulant such as a glycosaminoglycan and having activity as described above are combined to form a control solution having an anticoagulant concentration ranging from about 0.01 U/ml to about 0.15 U/ml, and preferably from about 0.01 U/ml to about 0.1 U/ml. Preferably, the human plasma and bovine plasma are combined with a heparinized buffer directly after thawing to form heparinized plasma solution that can be subsequently combined to form control solutions. According to another independent, but complementary method, a coagulation control composition is prepared by combining human plasma and non-primate mammalian plasma to form a control solution having non-primate mammalian plasma in an amount ranging from about 0.5% to about 12% by volume.

Preferred aspects of the invention additionally include methods for preparing a purified bovine plasma. In these methods, frozen bovine plasma is prepared or obtained (e.g. from commercial sources), thawed in an environment (e.g. a refrigerator) maintained a temperature ranging from about 2° C. to about 8° C. to allow particulates to form and come out of solution, and then treated to remove the particulates from the thawed bovine plasma. The freezing and cold-temperature thawing is preferably repeated at least once.

The invention is further directed to methods for evaluating a PT or APTT assay system. Such quality control methods generally include combining a PT reagent or an APTT reagent with a coagulation control to form an assay solution, detecting clot formation in the assay solution, and determining the time elapsed from formation of the assay solution to detection of clot formation in the assay solution. A comparison of the determined times can then be made with target times for the particular control being evaluated. For evaluation of a PT assay system, the coagulation control comprises a plasma and an anticoagulant having activity for enhancing the activity of antithrombin III (ATIII) and/or of heparin co-factor II (HCII) against thrombin and/or against blood clotting factors such as factors IXa, Xa and/or XIa. The anticoagulant is preferably a glycosaminoglycan and most preferably heparin, a heparin derivative or a heparin analog. For evaluation of either PT or APTT assay systems, the coagulation control comprises an abnormal plasma and anticoagulant such as a glycosaminoglycan having activity as described above. Alternatively, the coagulation control used for quality control of either PT or APTT assay systems comprises primate plasma, non-primate mammalian plasma and an anticoagulant such as a glycosaminoglycan having activity as described above.

The coagulation controls and methods of the present invention offer significant advantages over prior art control materials and methods. Controls disclosed and claimed herein have exceptional stability in reconstituted form, even when prepared in large-scale commercial production facilities. The controls can be prepared from readily available materials, using conventional equipment, under FDA good manufacturing practices. As such, the coagulation controls of the invention offer a commercially attractive alternative to existing coagulation controls for use in connection with PT and APTT assays.

Other features, objects and advantages of the present invention will be in part apparent to those skilled in the art and in part pointed out hereinafter. All references cited in the instant specification are incorporated by reference. Moreover, as the patent and non-patent literature relating to the subject matter disclosed and/or claimed herein is substantial, many relevant references are available to a skilled artisan that will provide further instruction with respect to such subject matter.

DETAILED DESCRIPTION OF THE INVENTION

Figure 1A:
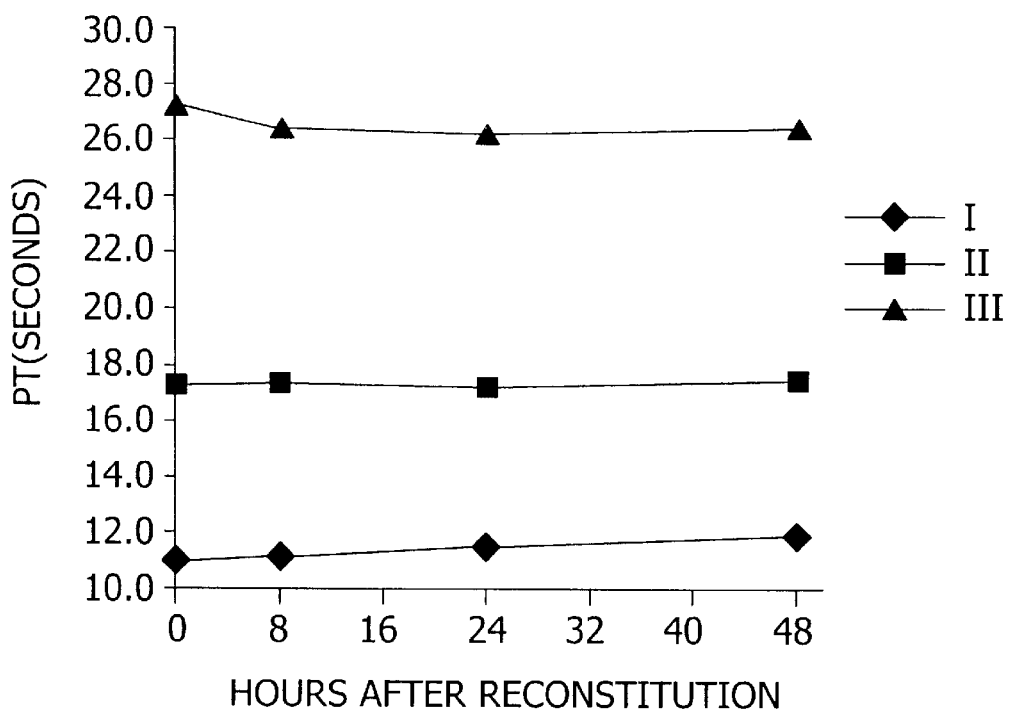
FIG. 1A and FIG. 1B are graphical representations of prothrombin time (PT) stability data for Level I, Level II and Level III coagulation controls prepared according to the methods of the present invention, and stored, after being reconstituted, at 2–8° C. Data was collected on an Amelung AMAX CS-190 coagulation analyzer using a PT reagent with an ISI value of 2.0 (Sigma ThromboMAX™) based on both optical (FIG. 1A) and mechanical (FIG. 1B) assays.

In the present invention, coagulation controls having enhanced stability over time—as demonstrated by consistent clotting times in PT and APTT assays and by the substantial absence of particulate and/or fibrin matter—are prepared by the addition of an agent having anticoagulant activity to the one or more plasmas being used in the control compositions. Plasmas are fairly unstable due to their large number of enzymes and their complex nature. As such, the anticoagulant is preferably added early in the production process to mitigate any activation of these enzymes that inherently occurs during production processes. Such an approach is a significant advance in the art—particularly for producing coagulation controls on a commercial scale. The manipulations inherent in large-scale production processes were not heretofore recognized in the art as being a causative factor for the observed instabilities of coagulation controls. Moreover, the art has not, heretofore, offered a solution to this problem.

Hence, according to one aspect of the invention, a coagulation control composition suitable for use in connection with PT and/or APTT assays is prepared by combining a plasma and an anticoagulant. Preferably, both a primate plasma (e.g. human plasma) and a non-primate mammalian plasma (e.g. bovine plasma) are combined with an anticoagulant. Preferred anticoagulants are those having activity for enhancing the activity of antithrombin III (ATIII) and/or of heparin co-factor II (HCII) against thrombin and/or against blood clotting factors such as factors IXa, Xa and/or XIa. The anticoagulant is preferably a glycosaminoglycan such as heparin, a heparin derivative and/or a heparin analog having anticoagulant activity. See Example 1. Without being bound by theory not specifically recited in the claims, glycosaminoglycan anticoagulants are advantageous over other coagulation-affecting moieties such as protease inhibitors because of differences in their anticoagulation mechanism. Whereas protease inhibitors such as aprotinin operate directly to inhibit particular blood clotting factors, glycosaminoglycan anticoagulants such as heparin, heparin derivatives and heparin analogs operate indirectly—with their inhibitory effect on blood clotting factors being mediated through intermediaries such as antithrombin III (ATIII) and/or heparin-cofactor II (HCII). As such, the glycosaminoglycan anticoagulants have a more subtle effect, but are still effective against a broad spectrum of blood clotting factors. Hence, the glycosaminoglycan anticoagulating agents are particularly useful for enhancing the stability of control compositions.

According to another aspect of the invention, human plasma is combined with relatively small amounts of non-primate mammalian plasma as compared to known compositions. Specifically, coagulation control compositions are prepared by combining human plasma and not more than about 12% by volume of non-primate mammalian plasma, and preferably from about 0.5% to about 12% by volume. Employing at least some non-primate mammalian plasma in the coagulation control offers an advantageous approach for controlling PT and APTT times, as described in more detail below. Advantageously, compositions having about 12% or less non-primate mammalian plasma remain stable with respect to both PT and APTT assays. However, compositions having more than about 12% non-primate mammalian plasma are unstable with respect to the PT assay.

As used herein, the term "plasma" generally refers to a solution comprising proteins and having procoagulant activity when combined with a prothrombin time (PT) reagent or with an activated partial thromboplastin reagent (APTT). Proteins in the plasma preferably include: blood clotting-factors involved with the extrinsic pathway (e.g. factor VII) and/or with the intrinsic pathway (e.g. factors XII, XI, IX and/or VIII); blood-clotting factors common to both pathways (e.g. factors X, II and/or V); thrombin; and fibrinogen. The plasma preferably also includes other plasma proteins, sugars, and/or salts. The plasma can be whole plasma that is obtained from humans or other animals. The plasma can also be a plasma derivative that has procoagulant activity and is derived from one or more whole plasmas. The plasma derivative can be, for example, a plasma fraction or a plasma that has been purified or otherwise treated to remove some protein, sugar, salt or other components thereof. The plasma can alternatively be a plasma substitute formed from components obtained from separate sources, including natural or man-made components, and having procoagulant activity. Exemplary man-made components include plasma proteins that are substantially isolated and/or purified from natural sources and plasma proteins that are prepared using recombinant technology. Whole plasmas, plasma derivatives and plasma substitutes are commercially available and/or can be prepared using methods presently known and/or later developed in the art.

One preferred plasma in the coagulation control is a primate plasma, and preferably a human plasma. The primate plasma can be a normal primate plasma or an abnormal primate plasma. Normal primate plasmas such as normal human plasmas (NHP) are plasmas obtained from individuals or other primates without clotting deficiencies. If evaluated using a PT assay with a thromboplastin reagent having an International Sensitivity Index of about 2, normal human plasmas would preferably have a clotting time ranging from about 9 seconds to about 14 seconds, preferably from about 11 seconds to about 13 seconds, and would most preferably be about 12 seconds. If evaluated using an APTT assay using an APTT reagent that is moderately sensitive to heparin and to lupus anticoagulant (e.g. Sigma APTT-FSL, Sigma Chemical, St. Louis, Mo.) and a suitable coagulation analyzer (e.g. Amelung AMAX CS-190), normal human plasmas would preferably have a clotting time ranging from about 22 seconds to about 32 seconds. Normal primate plasmas are typically treated with an anticoagulant such as citrate upon collection, and then frozen at a temperature ranging from about −50° C. to about −100° C. for storage. If frozen normal primate plasmas are employed as starting materials, they are preferably thawed in an environment (e.g. such as a water bath) at a temperature of about 37° C. prior to use in connection with the present invention. The normal primate plasmas are preferably pooled normal primate plasmas prepared by pooling of at least about 5, preferably at least about 10 plasma specimens obtained from individuals or other primates without clotting deficiencies. The normal primate plasmas can be pooled prior to freezing, or, if frozen prior to pooling, after thawing.

An abnormal plasma can, in general, be any plasma that is deficient with respect to clotting time as compared to a normal plasma. The deficiency can be an increased clotting time or a decreased clotting time, relative to normal plasma. An abnormal plasma can be a plasma collected from individuals, other primates or non-human mammals having naturally occurring clotting deficiencies or undergoing anticoagulant treatment. The abnormal plasma can also, however, have clotting deficiencies that are artificially induced by treatment of the plasma in vitro using methods known in the art.

Exemplary abnormal plasmas include activated plasmas—typically having lower-than-normal clotting times and employed in a coagulation control composition to decrease the clotting time of the control, and factor-deficient plasmas—typically having higher-than-normal clotting times and employed in a coagulation control composition to increase the clotting time of the control. As used herein, the term "activated plasma" refers to an abnormal plasma having increased levels of clotting factor Xa relative to normal plasma. An activated plasma can be human plasma or non-human plasma such as non-human primate plasma or non-primate mammalian plasma. An activated human plasma is a preferred activated plasma. The activated plasma can be activated for the extrinsic pathway (e.g. using thromboplastin and/or other known extrinsic-pathway activating agents) and/or for the intrinsic pathway (e.g. by exposing the plasma to intrinsic-pathway activating agents such as negatively charged moieties with a large surface area). Exemplary intrinsic-pathway activating agents include organic acid salts such as salts of ellagic acid, and silica-containing species such as micronized silica, kaolin, celite and glass-wool. The activated plasma is preferably a glass-wool activated plasma. As used herein, the term "factor-deficient plasma" refers to an abnormal plasma that is deficient in one or more clotting factors selected from the group consisting of factor II, factor VII, factor IX and/or factor X. Factor-deficient plasmas can be naturally occurring and obtained by collection from individuals or other mammals, or alternatively, can be induced in vitro by removing clotting factors from normal plasma by methods known in the art. In a preferred approach, factor-deficient plasmas are prepared by contacting the plasma with absorbents such as aluminum hydroxide, barium chloride, barium citrate, and/or barium sulfate, among others. Other methods can also be employed for preparing factor-deficient plasmas. For example, a factor VII-deficient plasma can be prepared using anti-factor VII antibodies and immunoaffinity purification protocols.

The primate plasma, preferably a human plasma, is generally present in a coagulation control solution in an amount ranging from about 25% to about 99.55%, more preferably in an amount ranging from about 50% to about 99.5%, even more preferably in an amount ranging from about 75% to about 99.5%, and most preferably in an amount ranging from about 78% to about 99.8% by volume, relative to total solution volume. The particular amount of primate (e.g. human) plasma will depend, as discussed below, on the types and quality of primate plasmas (e.g. normal and/or abnormal plasmas), on the presence of other types of plasmas (e.g. non-primate mammalian plasmas), and the type of control composition being prepared (e.g. Level I, II or III).

Another preferred plasma in the coagulation control is a non-primate mammalian plasma. Preferred non-primate mammalian plasmas for use in connection with the present invention include bovine plasma, swine plasma, goat plasma, sheep plasma, equine plasma and rabbit plasma, among others. Bovine plasma is a most preferred non-primate mammalian plasma. The non-primate mammalian plasma is preferably a normal plasma, but can also be an abnormal plasma such as a factor-deficient plasma and/or an activated plasma. Normal bovine plasma and normal plasmas from other non-primate mammals are typically obtained from animals without clotting deficiencies, and can be citrated upon collection, pooled and/or frozen for storage.

The non-primate mammalian plasmas are preferably purified prior to use in connection with the present invention. Frozen non-primate mammalian plasma, such as frozen bovine plasma, is either prepared or obtained, for example, from a commercial source. The frozen plasma is then thawed in an environment maintained at a temperature ranging from about 2° C. to about 8° C. Certain plasma constituents (e.g. plasma proteins) are not soluble at these cold temperatures, and as such, will fall out of solution, as precipitants and/or as particulates. The particulates formed in the thawed plasma are then removed therefrom by any suitable separation means, such as filtration or centrifugation. These freezing and thawing steps are then preferably repeated at least once, and preferably two or more times, by refreezing the partially-purified plasma, rethawing the refrozen plasma at a temperature ranging from about 2° C. to about 8° C., and then removing any additional particulates formed in the rethawed plasma. The resulting purified non-primate mammalian plasma is advantageously free of constituents (e.g. plasma proteins) that are insoluble at lower temperatures. Significantly, thawing at the recited cold temperatures allows for removal of such particulates prior to lyophilization. If the frozen plasma were thawed at higher temperatures, those particulates would have remained in solution and would have been included in the lyophilized composition. When such lyophilized composition were subsequently reconstituted, many of those particulates would not have resolubilized, and would, therefore, have been undesirably present as particulates in the reconstituted control composition.

The non-primate mammalian plasma is generally present in a coagulation control solution in an amount ranging from about 0.5% to about 12%, more preferably in an amount ranging from about 1% to about 10%, even more preferably in an amount ranging from about 1% to about 8%, still more preferably in an amount ranging from about 1% to about 6%, yet even more preferably in an amount ranging from about 2% to about 5%, and most preferably in an amount ranging from about ranging from about 2% to about 4% by volume, relative to total solution volume. The non-primate mammalian plasma is preferably present in an amount of about 3% by volume, relative to total solution volume. Advantageously, the non-primate mammalian plasma, and particularly bovine plasma, can be employed within the recited ranges to control PT and APTT times. For example, an increase in the amount of non-primate mammalian plasma within the recited ranges increases the PT while decreasing the APTT, and enhances the stability of the APTT. See Example 2. The use of relatively low-levels of non-primate mammalian plasma in a control composition can be independent of, or complementary with, the use of anticoagulants such as glycosaminoglycans.

Glycosaminoglycans are heteropolysaccharides comprising repeating disaccharide units containing a hexosamine residue and a hexose or hexuronic acid residue. The hexosamine residue can be an N-acetylhexosamine. Either or both of the residues may be sulfated. Preferred glycosaminoglycans include heparin, heparin derivatives, and/or heparin analogs. Heparin is a most preferred glycosaminoglycan. Heparin can be unfractionated heparin, a high molecular weight heparin or a low molecular weight heparin or combinations of various selected heparin fractions. The heparin derivative can be any heteropolysaccharide prepared from heparin, or chemically synthesized to comprise heparin-type disaccharide subunits, and having activity for enhancing the antithrombin activity of antithrombin III (ATIII) and/or heparin cofactor II (HCII). The heparin derivatives are preferably at least about five saccharide units in length, more preferably at least about eight saccharide units in length and most preferably at least about eighteen saccharide units in length, and also preferably include key sequence domains that confer anticoagulant activity on the heparin derivative—by enhancing the interaction of antithrombin III (ATIII) with clotting factors IXa, Xa and/or XIa, and/or by enhancing the interaction of ATIII and/or heparin cofactor II (HCII) with thrombin. See Rosenberg et al., *The Heparin-Antithrombin System: A Natural Anticoagulant Mechanism*, Chapter 41, pp.837–860 of the text *Hemostasis and Thrombosis: Basic Principles and Clinical Practice*, 3d Ed., ed. by R. Coleman et al., J. B. Lippincott Company, Philadelphia (1994). Exemplary heparin derivatives include, for example, enzyme-treated heparin, such as the chondroitinase-treated heparin disclosed in copending U.S. Pat. No. 5,985,582 which is effective for enhancing the antithrombin III activity against thrombin, but which is less effective than unmodified heparin for enhancing the heparin cofactor II activity against thrombin. Preferred heparin analogs include heparan sulfate, dermatan sulfates, chondroitin sulfates, keratan sulfates, mesoglycan, sulodexide, and hyaluronic acid. The heparin analogs also include other glycosaminoglycans having anticoagulant activity, and particularly, having activity for enhancing the antithrombin activity of ATIII and/or HCII, and/or for enhancing the interaction between ATIII and clotting factors IXa, Xa and/or XIa. Heparin and heparin analogs can be obtained from many commercial sources. Heparin derivatives can also be obtained commercially and/or prepared according to protocols known or later developed in the art. See Oosta et al., *Multiple Functional Domains of the Heparin Molecule*, Proc. Natl. Acad. Sci. USA, 78:829 (1981).

The concentration of anticoagulants such as glycosaminoglycans in a coagulation control solution preferably ranges from about 0.01 U/ml to about 0.15 U/ml, more preferably from about 0.01 U/ml to about 0.1 U/ml, even more preferably from about 0.03 U/ml to about 0.07 U/ml, and is most preferably about 0.05 U/ml, where U is heparin-equivalent units as defined below and ml is milliliters of the coagulation control solution. These concentrations are recited as preferred in the control solution as it is used—regardless of whether the solution is an as-prepared solution or a solution reconstituted from a solid (e.g. lyophilized) composition. The corresponding concentration of glycosaminoglycan in a solid composition preferably ranges from about 0.1 U/g to about 1.8 U/g, more preferably from about 0.3 U/g to about 1.2 U/g, even more preferably from about 0.4 U/g to about 0.8 U/g, and is most preferably about 0.6 U/g, on a dry-weight basis where U is heparin-equivalent units. Other concentrations in the solid composition can be employed, however, with adjustments as necessary to achieve a control solution having the above-recited preferred concentrations of anticoagulants in the control solution. As noted, the units, U, of the glycosaminoglycan are recited herein as heparin-equivalent units. That is, the unit, U, represents the amount of a given anticoagulant (e.g. glycosaminoglycan) sufficient to have an anticoagulant activity, preferably an anti-factor X activity, that is about equal to the anticoagulant activity, preferably the anti-factor X activity, of normal, unfractionated heparin (UFH) at the recited numeric values. Hence, for unfractionated heparin and for heparin fractions or heparin derivatives having the same specific activity (by weight or volume as appropriate) as unfractionated heparin, the recited numeric values represent actual units of heparin activity, $U_{hep}$, with one unit of heparin activity being defined as per the United States Pharmacopeia (USP). See also Yin et al., *Heparin-Accelerated Inhibition of Activated Factor X by Its Plasma Inhibitor*, Biochem. Biophys. Acts 201:387 (1970); Yin et al., *Plasma Heparin: A Unique, Practical Submicrogram Sensitive Assay*, J. Lab. Clin. Med., 81:298 (1973). In contrast, however, for heparin analogs, some heparin fractions, heparin derivatives or other anticoagulants that have a different specific activity (by weight or volume, as appropriate) than unfractionated heparin, the amounts thereof should be sufficient to effect the same level of anticoagulant activity as unfractionated heparin would effect, if the UHF were used at the recited concentration values. Equivalent anticoagulant activities are preferably determined by an assay for activity that involves a substrate that is common to both unfractionated heparin and the non-UHF glycosaminoglycan. For example, if the glycosaminoglycan is dermatan sulfate, heparin-equivalent activity can be determined using an assay that determines the glycosaminoglycan activity for clotting-factor Xa.

The coagulation control composition can include other components in addition to the primate plasma, non-primate mammalian plasma and anticoagulant. For example, the control composition preferably also includes buffers and bulking agents. The buffer can be any suitable buffer, and preferably has a $pK_a$ ranging from about 6 to 8, more preferably from about 7 to 8, and most preferably of about 7.1 to about 7.6. Preferred buffers include for example, N-2-hydroxyethyl piperazine-N-2-ethanesulfonic acid (HEPES), and 3-(N-morpholino)-propanesulfonic acid (MOPS), with HEPES being a most preferred buffer. Other exemplary buffers include Tris, N,N-bis-(hyrdroxyethyl)-2-aminoethanesulfonic acid (BES), N-tris-(hyrdroxymethyl)-methyl-2-aminoethanesulfonic acid (TES), 3-[N-tris (hydroxymethyl) methylamino]-2-hydroxypropanesulfonic acid (TAPSO) and 3-[N-tris-(hydroxymethyl-methylamino]-propanesulfonic acid (TAPS), among others. The amount of buffer included can be generally based on PT and/or APTT times, and preferably ranges from about 20 mM to about 200 mM, and is most preferably about 50 mM in the control solution. Bulking agents that can be included in the control composition include glycine, glucitol, mannitol, sorbitol, lactose, dextrose and the like. Glycine is a preferred bulking agent. Bulking agents are preferably included in an amount ranging from about 0.5% to about 5%, by weight, and is most preferably at about 1% by weight, relative to total solution weight assuming a solution density of about 1 gml. That is, 1% bulking agent by weight is equal to 10 g bulking agent per liter of solution. Stabilizers, preservatives, and other components known in the art can also be employed in the coagulation control composition. Stabilizers that may be useful include, for example, Goods buffers, Tris, bovine serum albumin (BSA), piperazine-N,N-bis(2-ethane-sulfonic acid, 1.5 sodium salt (PIPES), imidazole, 3-(N-morpholino)-2-hydroxypropanesulfonic acid (MOPSO), MOPS, BES, TES, HEPES, TAPSO, TAPS, 3-[N-bis(hydroxyethyl) amino]-2-hydroxypropanesulfonic acid (DIPSO), piperazine-N,N'-bis (2-hydroxypropanesulfonic acid (POPSO), N-hydroxyethyl piperazine-N'-2-hydroxypropanesulfonic acid (HEPPSO), tricine and bicine. Preservatives that may be helpful for preventing the growth of microorganisms, such as antifungal, antibacterial and antiyeast compositions, may also be included in the composition. Exemplary preservatives include organic acids such as propionic acid, sodium azide, thimerosal, BHA, BHT and preformulated multiactivity formulations such as ProClinTM. The concentrations of these additional composition components can be determined and optimized by a person of skill in the art. The total volume contribution of such additional components to a coagulation control solution can, in general, range from about 0%–3%, and preferably from about 0%–2% by volume, relative to total solution volume. Control compositions typically include about 1% of such other constituents, by volume, relative to total solution volume.

The primate plasma and non-primate mammalian plasma are preferably combined, relative to each other, in amounts sufficient to achieve the desired prothrombin time (PT) and/or activated partial thromboplastin time (APTT) coagulation times for Level I, Level II or Level III controls—preferably, but not necessarily, in a final composition that includes a glycosaminoglycan in the above-recited concentration ranges. In general, the coagulation control can have a PT ranging from about 9 seconds to about 35 seconds, and an APTT ranging from about 20 seconds to about 100 seconds. In particular, for a Level I coagulation control composition, the PT preferably ranges from about 9 seconds to about 14 seconds, more preferably from about 11 seconds to about 13 seconds, and is most preferably about 12 seconds. The APTT for a Level I control preferably ranges from about seconds to about 34 seconds, more preferably from about 22 seconds to about 32 seconds, and is most preferably about 30 seconds. For a Level II coagulation control, the PT preferably ranges from about 15 seconds to about 25 seconds, more preferably from about 17 seconds to about 22 seconds, and is most preferably about seconds. The APTT for a Level II control preferably ranges from about 40 seconds to about 60 seconds, more preferably from about 47 seconds to about 53 seconds, and is most preferably about 50 seconds. For a Level III coagulation control, the PT preferably ranges from about 25 seconds to about 33 seconds, more preferably from about 27 seconds to about 31 seconds, and is most preferably about 28 seconds. The APTT for a Level III control preferably ranges from about 70 seconds to about 100 seconds, more preferably from about 75 seconds to about 85 seconds, and is most preferably about 78 seconds. Each of the aforementioned PT assay times are preferably determined using a thromboplastin reagent having an International Sensitivity Index (ISI) of about 2, such as ThromboMAX™ (Sigma, St. Louis, Mo.). Each of the aforementioned APTT assay times are preferably determined using an APTT reagent that is moderately sensitive to heparin and to lupus anticoagulant (Sigma APTT-FSL) as the APTT reagent and using a suitable analyzer (e.g. AMAX CS-190).

The primate plasma and non-primate mammalian plasma are generally combined, relative to each other, such that the ratio of non-primate mammalian plasma to primate plasma ranges from about 1:200 to about 1:5, more preferably ranges from about 1:200 to about 1:10 and most preferably ranges from about 1:50 to about 1:20, by volume (for a control solution) or by weight (for a control composition in lyophilized form). A coagulation control solution preferably comprises primate plasma such as human plasma in an amount ranging from about 78% to about 99.5% by volume, and a non-primate mammalian plasma such as bovine plasma present in an amount ranging from about 0.5% to about 12% by volume. The most preferred ratios and or volume percents for particular control levels will vary depending on the type and quality of primate or human plasma (e.g. normal human plasma versus abnormal human plasma, and type of abnormal plasma) and on the type and quality of non-primate mammalian plasma (e.g. bovine versus swine; normal versus abnormal) employed in the coagulation composition.

The anticoagulant is preferably added to the plasma solutions as a first step (e.g. immediately after collection or immediately after thawing of the plasmas), or at least as an early step in the preparation of the coagulation control. Without being bound by theory not specifically recited in the claims, early addition of the anticoagulant (e.g. heparin) will enhance the anticoagulation activity of plasma constituents such as antithrombin III and heparin cofactor II, and will thereby preclude and/or mitigate the activation of clotting factors. While the following approaches are described with respect to human plasmas and with respect to glycosaminoglycans, they are equally applicable to the forming of control compositions with other primate plasmas and with other anticoagulants. In a preferred approach, the human plasma is combined with the glycosaminoglycan to form a human plasma solution, the non-primate mammalian plasma is combined with the glycosaminoglycan to form a non-primate mammalian plasma solution, and the human plasma solution and the non-primate mammalian plasma solution are then combined.

In this preferred approach, the concentration of the glycosaminoglycan in the human plasma solution and the non-primate mammalian plasma solution is preferably the same in each such solution and preferably equal to the target concentration for the coagulation control, but could, if desired however, be different in each solution. Where one or more of the plasmas are treated, for example, to be purified, the heparin can likewise be added before such treatment.

In general, however, other approaches could also be employed for combining the primate plasma, non-primate mammalian plasma and glycosaminoglycan. In one alternative approach, for example, the human plasma is first combined with the non-primate mammalian plasma to form a plasma mixture, and the glycosaminoglycan is then combined with the plasma mixture. In another alternative approach, the human plasma is combined with the glycosaminoglycan to form a human plasma solution, and the human plasma solution is then combined with the non-primate mammalian plasma. In a similar approach, the non-primate mammalian plasma is combined with the glycosaminoglycan to form a non-primate mammalian plasma solution, and the non-primate mammalian plasma solution is then combined with the human plasma.

In any of the aforementioned approaches, the glycosaminoglycan, typically a solid in its commercially-available form, is preferably solubilized in a buffer before being combined with the human plasma and/or with the non-primate mammalian plasma. Pre-solubilizing the glycosaminoglycan in the buffer rather than directly in the plasma avoids extensive mixing required to solubilize the same in the plasma, and thereby helps avoid activation of plasma enzymes. The bulking agents (e.g. glycine), stabilizers and/or preservatives can be added to heparinized plasma solutions either before or after such solutions are combined.

Preferred coagulation control compositions comprise normal human plasma, bovine plasma, and either heparin or a heparin derivative. While preferred Level I, Level II and Level III controls are described below with reference to bovine plasma as the non-primate mammalian plasma and with reference to heparin or a heparin derivative as the glycosaminoglycan, it is to be understood that other non-primate mammalian plasmas and other glycosaminoglycans could be equivalently substituted in such description. Such substitution is within the ordinary skill in the art in view of the guidance provided herein. Moreover, while preferred relative amounts of the various plasma components are set forth below for Level I, II and III coagulation control compositions, optimal combinations of the various plasma solutions outside the recited ranges, but still falling within the scope of the invention, can also be developed by those skilled in the art.

A preferred Level I coagulation control comprises normal human plasma, normal bovine plasma, heparin or a heparin derivative, one or more buffers, and optionally, an activated plasma, a bulking agent, a preservative and/or a stabilizer. See Example 3. According to a preferred method, the preferred control Level I is prepared by solubilizing heparin or a heparin derivative into a buffer, and then combining the buffered heparin (or buffered heparin derivative) with normal human plasma to form a heparinized human plasma solution comprising heparin or heparin derivative at a concentration ranging from about 0.01 U/ml to about 0.15 U/ml. A bulking agent can also be included in the heparinized bovine plasma solution. In a similar manner, the buffered heparin (or buffered heparin derivative) is combined with bovine plasma, purified as described above, to form a heparinized bovine plasma solution comprising heparin or heparin derivative at a concentration ranging from about 0.01 U/ml to about 0.15 U/ml. A bulking agent can also be included in the heparinized human plasma solution. If desired to be used in the control composition, an activated plasma is preferably prepared from the heparinized normal human plasma solution. For example, a glass-wool activated plasma can be prepared by contacting the heparinized human plasma solution with glass wool for a period of time ranging from about 12 hours to about 30 hours, and preferably for a period of about 15 hours to 18 hours at a temperature ranging from about 2° C. to about 8° C. A bulking agent can be added to the heparinized activated plasma solution. The heparinized normal human plasma solution, the heparinized bovine plasma solution and, if included, the heparinized activated plasma solution, are then combined in appropriate relative amounts to form a Level I control composition having the desired PT and APTT values.

The heparinized plasma solutions are preferably combined in relative proportions to form a Control Level I solution comprising normal human plasma in an amount ranging from about 78% to about 99.5%, by volume, bovine plasma in an amount ranging from about 0.5% to about 12%, by volume, activated plasma in an amount not more than about 7%, by volume, with other components (e.g. buffers, bulking agents, etc) amounting to not more than about 3% by volume. The heparinized plasma solutions are more preferably combined in relative proportions to form a Control Level I solution comprising normal human plasma in an amount ranging from about 86% to about 99%, by volume, bovine plasma in an amount ranging from about 1% to about 6%, by volume, activated plasma in an amount not more than about 5%, by volume, with other components (e.g. buffers, bulking agents, etc) amounting to not more than about 2% by volume. The heparinized plasma solutions are most preferably combined in relative proportions to form a Control Level I solution comprising normal human plasma in an amount ranging from about 88% to about 95%, by volume, bovine plasma in an amount ranging from about 2% to about 4%, by volume, activated plasma in an amount ranging from about 3% to about 5%, by volume, with other components (e.g. buffers, bulking agents, etc) ranging from about 1% to about 2% by volume.

Preferred Level II and Level III coagulation controls comprise normal human plasma, normal bovine plasma, factor-deficient plasma, heparin or a heparin derivative, one or more buffers, a bulking agent, and optionally, a preservative and/or a stabilizer. See Example 4 (Level II) and Example 5 (Level III). The preferred Control Level II and Control Level III are prepared by forming a heparinized human plasma solution from normal human plasma and by forming a heparinized bovine plasma solution as described above for the Level I Control. A heparinized factor-deficient plasma solution is also prepared, preferably from the heparinized normal human plasma solution by absorbing the same with an absorbent, preferably with aluminum hydroxide, according to known methods. The heparinized normal human plasma solution, the heparinized bovine plasma solution and the heparinized factor-deficient plasma solution are then combined in appropriate relative amounts to form either a Level II control composition or a Level III control composition having the respectively desired PT and APTT values.

To form a preferred Level II control composition, these heparinized plasma solutions are preferably combined in relative proportions to form a control solution comprising factor-deficient plasma in an amount ranging from about 75% to about 85%, by volume, bovine plasma in an amount ranging from about 0.5% to about 12%, by volume, and normal human plasma in an amount ranging from about 0.5% to about 24.5%, by volume, with other components (e.g. buffers, bulking agents, etc) amounting to not more than about 3% by volume. The heparinized plasma solutions are more preferably combined in relative proportions to form a Control Level II solution comprising factor-deficient plasma in an amount ranging from about 77% to about 83%, by volume, bovine plasma in an amount ranging from about 1% to about 6%, by volume, and normal human plasma in an amount ranging from about 8% to about 22%, by volume, with other components (e.g. buffers, bulking agents, etc) amounting to not more than about 2% by volume. The heparinized plasma solutions are most preferably combined in relative proportions to form a Control Level II solution comprising factor-deficient plasma in an amount ranging from about 78% to about 82%, by volume, bovine plasma in an amount ranging from about 2% to about 4%, by volume, and normal human plasma in an amount ranging from about 11% to about 20%, by volume, with other components (e.g. buffers, bulking agents, etc) ranging from about 1% to about 2%, by volume.

A preferred Level III control composition is formed by combining these heparinized plasma solutions in relative proportions to form a control solution comprising factor-deficient plasma in an amount ranging from about 85% to about 95%, by volume, bovine plasma in an amount ranging from about 0.5% to about 12%, by volume, and normal human plasma in an amount ranging from about 0.5% to about 14.5%, by volume, with other components (e.g. buffers, bulking agents, etc) amounting to not more than about 3% by volume. The heparinized plasma solutions are more preferably combined in relative proportions to form a Control Level III solution comprising factor-deficient plasma in an amount ranging from about 87% to about 93%, by volume, bovine plasma in an amount ranging from about 1% to about 6%, by volume, and normal human plasma in an amount ranging from about 0.5% to about 12%, by volume, with other components (e.g. buffers, bulking agents, etc) amounting to not more than about 2% by volume. The heparinized plasma solutions are most preferably combined in relative proportions to form a Control Level III solution comprising factor-deficient plasma in an amount ranging from about 88% to about 92%, by volume, bovine plasma in an amount ranging from about 2% to about 4%, by volume, and normal human plasma in an amount ranging from about 1% to about 10%, by volume, with other components (e.g. buffers, bulking agents, etc) ranging from about 1% to about 2%, by volume.

Coagulation control solutions prepared as described above can be lyophilized according to methods known in the art. For example, the compositions can be lyophilized by freezing at a temperature and under vacuum for a period of time sufficient to form the lyophilized control composition. The temperature, vacuum and period of time are not narrowly critical, but lyophilization can be generally performed as follows. The compositions are frozen to a deep freeze temperature typically ranging from about −60° C. to about −20° C. without vacuum for a period of time ranging from about 2 hours to about 24 hours. A vacuum is then applied, preferably ranging from about 10 millitorr to about 200 millitorr absolute pressure. The shelf temperature is then raised somewhat, typically to a temperature ranging from about 0° C. to about 25° C., for a period of time sufficient to lyophilize the composition. The lyophilization is, more preferably, performed by first deep-freezing the composition in a chamber to a temperature of about −40° C. without vacuum for a period of about 4 hours, then drawing a vacuum in the chamber of less than about 200 millitorr, and subsequently raising the temperature preferably to about 25° C. for a period sufficient for the product to reach about 25° C. for about 4 hours. In a preferred embodiment, about 1 ml to about 5 ml, and preferably about 1 ml to about 3 ml of a the control solution is supplied to a vial and lyophilized by freezing for about 4 hours at −40° C. without vacuum. A vacuum of less than about 200 millitorr is subsequently applied, and the shelf temperature is raised to about 25° C. for a period of time sufficient to lyophilize the solution. The lyophilized composition is preferably sealed under vacuum. The lyophilized composition can be stored, prior to reconstituting, for about 2 years at temperatures from about 2° C. to about 8° C.

The lyophilized control composition can be reconstituted using water, an appropriate buffer or other reconstituting solution. Preferably, the volume of reconstituting solution is sufficient to form coagulation control solutions comprising the various plasmas at the aforementioned relative volumes. If desired to use a larger or smaller reconstituting volume, the amounts of the various plasmas present in the as-prepared control solutions, prior to lyophilization, should be adjusted accordingly to form a post-lyophilization, reconstituted coagulation control solutions comprising the various plasmas at the aforementioned relative volumes.

The reconstituted coagulation control compositions of the present invention have enhanced stability with respect to both PT and APTT assays. As demonstrated in Example 6, for example, Level I, Level II and Level III controls prepared as described and claimed herein have excellent stability up to 48 hours after being reconstituted—about six times longer than current commercially available controls.

The coagulation controls described above can be used to evaluate PT and/or APTT assay systems for quality control purposes. Such quality control methods generally include combining a PT reagent or an APTT reagent with one of the afore-described coagulation controls to form an assay solution, detecting clot formation in the assay solution, and determining the time elapsed from formation of the assay solution to detection of clot formation in the assay solution. For evaluation of a PT assay system, the coagulation control can comprise an anticoagulant and any suitable plasma. For evaluation of either PT or APTT assay systems, the coagulation control comprises, according to one approach, an anticoagulant and an abnormal plasma. In another approach for quality control of PT or APTT assay systems, the coagulation control comprises primate plasma, non-primate mammalian plasma and an anticoagulant.

Prothrombin time (PT) reagents, as used herein, refers to a solution comprising tissue factor and cationic ions, preferably calcium ions ($Ca^{++}$). Tissue factor is an integral membrane glycoprotein that is biologically active for initiating blood coagulation through the extrinsic pathway. Tissue factor comprises a protein component, tissue factor protein, and a lipid component. The lipid component of tissue factor primarily comprises phospholipids. Tissue factor can be naturally occurring tissue factor, such as that included in mammalian tissue extracts, or, alternatively, can be synthetically prepared, for example, by combination of isolated or recombinantly produced tissue factor protein and phospholipids at appropriate ratios. See U.S. Pat. No. 5,017, 556 and references cited therein.

Activated partial thromboplastin time (APTT) reagents, as used herein, refers to a solution comprising the lipid component of tissue factor, without tissue factor protein, and an intrinsic-pathway activating agent. Intrinsic-pathway activating agents are typically negatively charged moieties with a large surface area, and can include, for example, organic acid salts such as salts of ellagic acid, and silica-containing species such as micronized silica, kaolin, celite and glass-wool.

Clot formation can be detected, and the time required for such clot formation can be determined, using manual and/or automated protocols. Exemplary methods for determination of clot formation include visual observations with a "tilt-tube" technique, electrochemical methods (e.g. fibrometer), optical methods (e.g. based on absorbance or rate of change of absorbance), among others. Exemplary automated analyzers include the AMAX CS-190 (Sigma Chemical, St. Louis, Mo.).

A comparison of the determined times can then be made with target ranges for the particular control being evaluated. Where the coagulation control is combined with a PT reagent, the determined time can be compared with the PT target times for the Level I, Level II and Level III controls, as set forth above. Where the coagulation control is combined with an APTT reagent, the determined time can be compared with the APTT target times for the Level I, Level II and Level III controls, as set forth above. Determined times that are outside of the target times are indicative of a quality control concern for the assay system. Such concerns typically relate to the PT/APTT reagent or to the device and/or protocols employed in determining the clotting time.

The following examples illustrate the principles and advantages of the invention.

EXAMPLES

Example 1

Effect of Heparin on Coagulation Controls

In order to test the effect of adding heparin to a coagulation control composition, three Level III control compositions, designated as Pilot No.'s A, B and C, were prepared and evaluated as follows.

A heparinized normal human plasma solution was prepared from normal human plasma. Frozen, citrated human plasma (3–4% citrate) was thawed in a water bath at 30–37° C. In Pilot No. A which served as an experimental control, HEPES buffer was added (without heparin) to the thawed plasma to a concentration of 50 mM HEPES. In Pilot No.'s B and C, HEPES buffer containing heparin was added to the thawed plasma to a concentration of 50 mM HEPES and 0.05 U/mL heparin to form a heparinized normal human plasma solution. In each case, the pH of the HEPES buffer was 7.2–7.4 and the buffer was prepared in advance as a 40x concentrate to minimize dilution effects when added to the plasma. The heparin was pharmaceutical grade heparin derived from bovine lung diluted to 1000 U/mL in 0.85% saline (Upjohn Co., Kalamazoo, mich. ).

A factor-deficient human plasma was prepared from a portion of the heparinized normal human plasma solution prepared above. Clotting factors II, VII, IX and X were absorbed by mixing the heparinized human plasma solution with aluminum hydroxide (25g/L) for 30–45 minutes at a temperature maintained at about 2–8° C. The alumina was removed by centrifugation.

A heparinized normal bovine plasma solution was also prepared. Frozen, citrated normal bovine plasma was thawed in a refrigerator maintained at a temperature ranging from about 2° C. to about 8° C., and then filtered using a coarse filter (Whitman #1) to remove precipitants and/or particulates that had formed during cold-temperature thawing. The freezing, thawing and removal of precipitated particulates was repeated. The purified bovine plasma was prepared in bulk and then stored at −70 °C. To prepare the heparinized bovine plasma solution, frozen purified bovine plasma was thawed in a water bath at a temperature of about 30° C. to about 37° C., and a HEPES buffer containing heparin was added to the thawed bovine plasma to a concentration of 50 mM HEPES and 0.05 U/mL heparin.

Level III control compositions were then prepared by combining the heparinized factor-deficient (absorbed) human plasma solution (about 89%, by volume), the heparinized normal human plasma solution (about 7%, by volume) and the heparinized bovine plasma solution (about 4%, by volume). In Pilot No. C, an additional 0.05 U/mL of heparin was added after combining of the various plasma solutions to bring the total heparin concentration to 0.1 U/mL. Glycine was added to each of the pilot compositions to 1%, by weight, and the pilots were then filled in vials and lyophilized.

Each of the pilots were subsequently evaluated using prothrombin time (PT) and activated partial thromboplastin time (APTT) assays after being reconstituted with water to the same volume as the prelyophilization volume at which the vials were filled.

For stability testing, the reconstituted samples were analyzed both immediately after reconstitution, and after storage on-board the analyzer at 15–22° C. for 24 hours and 48 hours. Data was collected on an Amelung AMAX CS-190 coagulation analyzer using a PT reagent with an ISI value of 2.0 (Sigma Thromboplastin-XS) and APTT reagent that is moderately sensitive to heparin and to lupus anticoagulant (Sigma APTT-FSL). Both mechanical and optical determinations were made.

The results are shown below for both PT assays (Table 1A) and APTT assays (Table 1B). The data shown in these tables demonstrate that coagulation controls comprising heparin added after thawing and prior to adsorption (Pilot No.'s B and C) were more stable than controls lacking heparin (Pilot No. A). Comparison of the data for Pilot No.'s B and C shows that heparin added after combination of the various plasmas further increased the APTT, but had little, if any, additional effect on stability.

TABLE 1A

Effect of Heparin on Coagulation Controls
(On-Board Stability Summary -- PT Data)

| | Lot Description | | | | | AMAX PT Data (TP-XS) | | | | | |
|---|---|---|---|---|---|---|---|---|---|---|---|
| | Factor- | Normal | Normal | | | PT (Optical) | | | PT (Mechanical) | | |
| | Deficient | Bovine | Human | | Heparin | | | | | | |
| Pilot No. | Human Plasma % | Plasma % | Plasma % | Heparin U/mL | Before Adsorb? | 0 hr secs | 24 hr % Diff | 48 hr % Diff | 0 hr secs | 24 hr % Diff | 48 hr % Diff |
| A | 89 | 4 | 7 | 0.00 | No | 24.1 | −4.6 | −5.0 | 26.5 | −6.4 | −7.1 |
| B | 89 | 4 | 7 | 0.05 | Yes | 25.0 | −0.7 | −1.1 | 28.6 | −2.4 | −3.8 |
| C | 89 | 4 | 7 | 0.10 | Yes | 25.1 | −2.4 | −2.8 | 28.2 | −3.2 | −6.1 |

TABLE 1B

Effect of Heparin on Coagulation Controls
(On-Board Stability Summary -- APTT Data)

| | Lot Description | | | | | AMAX APTT Data (APTT-FSL) | | | | | |
|---|---|---|---|---|---|---|---|---|---|---|---|
| | Factor- | Normal | Normal | | | APTT (Optical) | | | APTT (Mechanical) | | |
| | Deficient | Bovine | Human | | Heparin | | | | | | |
| Pilot No. | Human Plasma % | Plasma % | Plasma % | Heparin U/mL | Before Adsorb? | 0 hr secs | 24 hr % Diff | 48 hr % Diff | 0 hr secs | 24 hr % Diff | 48 hr % Diff |
| A | 89 | 4 | 7 | 0.00 | No | 58.2 | −0.3 | −2.3 | 69.8 | −1.4 | −4.9 |
| B | 89 | 4 | 7 | 0.05 | Yes | 61.5 | 0.8 | 1.6 | 72.8 | 0.7 | 1.4 |
| C | 89 | 4 | 7 | 0.10 | Yes | 66.9 | −3.0 | −2.0 | 80.3 | −4.1 | −3.3 |

Example 2

Effect of Bovine Plasma on Coagulation Controls

In order to test the effect of bovine plasma concentrations on coagulation control compositions, Level III control compositions having various relative amounts of factor-deficient human plasma, normal human plasma and bovine plasma were prepared and evaluated as follows.

A heparinized normal human plasma solution, a heparinized factor-deficient human plasma solution, and a heparinized normal bovine solution was prepared as described in Example 1. These plasma solutions were then combined in various relative amounts, as summarized in Table 2. Glycine was added to each of the compositions to 1%, by weight, and the control solutions were then filled in vials and lyophilized.

Each of the control compositions were subsequently evaluated using prothrombin time (PT) and activated partial thromboplastin time (APTT) assays after being reconstituted with water to the same volume as the volume at which the vials were originally filled prior to lyophilization. For stability testing, the reconstituted samples were analyzed both immediately after reconstitution, and after storage on-board the analyzer at 15–22° C. for 24 hours and 48 hours. Data was collected on an Amelung AMAX CS-190 coagulation analyzer using a PT reagent with an ISI value of 2.0 (Sigma Thromboplastin-XS) and APTT reagent that is moderately sensitive to heparin and to lupus anticoagulant (Sigma APTT-FSL). Both mechanical and optical determinations were employed.

The results are shown in Table 2 for both PT assays (Table 2A) and APTT assays (Table 2B). The data shown in Table 2 demonstrate that increased levels of bovine plasma increased the PT and decreased the APTT. While bovine plasma appears to protect the APTT stability and has little affect on PT stability at amounts of 11% or less, by volume, plasma at levels of 13% by volume appear to decrease the PT ability.

Example 3
Preparation of Level I Coagulation Controls

In order to prepare Level I coagulation controls suitable to mimic normal plasma, four Level I control compositions, designated as Pilot No.'s 1, 2, 3 and 4 were prepared and evaluated as follows.

Heparinized normal human plasma solution and heparinized normal bovine plasma solution, each comprising 0.05 U/ml heparin and 50 mM HEPES, were prepared from normal plasmas as described in Example 1, except that the heparin employed was a heparin sodium salt derived from bovine lung. (Sigma Chemical, St. Louis, Mo., Cat. No. H4898).

A heparinized activated plasma was prepared from a portion of the heparinized normal human plasma solution,

TABLE 2A

Effect of Bovine Plasma on Coagulation Controls
(On-Board Stability Summary -- PT Data)

| Lot Description | | | AMAX PT Data (TP-XS) | | | | | |
|---|---|---|---|---|---|---|---|---|
| Factor- | Normal | Normal | | | | | | |
| Deficient | Bovine | Human | PT (Optical) | | | PT (Mechanical) | | |
| Human Plasma % | Plasma % | Plasma % | 0 hr secs | 24 hr % Diff | 48 hr % Diff | 0 hr secs | 24 hr % Diff | 48 hr % Diff |
| 87 | 0 | 13 | 20.1 | 3.2 | 5.9 | 22.6 | −0.5 | 2.2 |
| 87 | 1 | 12 | 20.1 | 0.6 | 1.4 | 22.6 | −2.3 | 0.7 |
| 87 | 4 | 9 | 20.6 | −1.4 | −1.4 | 22.8 | −0.3 | −1.5 |
| 87 | 8 | 5 | 23.3 | −2.4 | −2.8 | 26.2 | −2.7 | −3.7 |
| 87 | 11 | 2 | 27.0 | −0.4 | −0.3 | 32.4 | −3.7 | −1.1 |
| 87 | 13 | 0 | 37.9 | −4.1 | −4.7 | 46.0 | −6.7 | −6.6 |
| 89 | 4 | 7 | 25.0 | −0.7 | −1.1 | 28.6 | −2.4 | −3.8 |
| 89 | 3 | 8 | 24.1 | −1.9 | −1.4 | 26.1 | −2.0 | −1.9 |
| 89 | 2 | 9 | 24.2 | −1.4 | −1.2 | 26.8 | −4.1 | −4.4 |
| 89 | 1 | 10 | 24.1 | −1.1 | −0.3 | 26.7 | −2.6 | −3.3 |
| 90 | 4 | 6 | 26.5 | −1.9 | −1.3 | 31.4 | −5.9 | −5.9 |
| 90 | 1 | 9 | 25.5 | −0.9 | −0.4 | 29.8 | −4.6 | −7.4 |

TABLE 2B

Effect of Bovine Plasma on Coagulation Controls
(On-Board Stability Summary -- APTT Data)

| Lot Description | | | AMAX APTT Data (APTT-FSL) | | | | | |
|---|---|---|---|---|---|---|---|---|
| Factor- | Normal | Normal | | | | | | |
| Deficient | Bovine | Human | APTT (Optical) | | | APTT (Mechanical) | | |
| Human Plasma % | Plasma % | Plasma % | 0 hr secs | 24 hr % Diff | 48 hr % Diff | 0 hr secs | 24 hr % Diff | 48 hr % Diff |
| 87 | 0 | 13 | 60.0 | −1.2 | 0.9 | 70.8 | −0.9 | 0.8 |
| 87 | 1 | 12 | 57.9 | −0.9 | 0.0 | 68.8 | −1.4 | −0.8 |
| 87 | 4 | 9 | 55.7 | −1.8 | −2.4 | 66.7 | −3.3 | −2.9 |
| 87 | 8 | 5 | 53.3 | 0.0 | −0.6 | 64.9 | −2.9 | −1.7 |
| 87 | 11 | 2 | 43.8 | 8.9 | 8.0 | 55.5 | 3.8 | 3.9 |
| 87 | 13 | 0 | 52.6 | 0.8 | 1.4 | 64.4 | 0.8 | 0.8 |
| 89 | 4 | 7 | 61.5 | 0.8 | 1.6 | 72.8 | 0.7 | 1.4 |
| 89 | 3 | 8 | 61.8 | 0.1 | 0.9 | 73.9 | −0.5 | −0.6 |
| 89 | 2 | 9 | 64.1 | 0.4 | 1.1 | 76.6 | −1.3 | −2.1 |
| 89 | 1 | 10 | 65.9 | 0.5 | 1.7 | 78.2 | −0.7 | 0.0 |
| 90 | 4 | 6 | 63.7 | 0.8 | 1.2 | 77.1 | −2.0 | −0.7 |
| 90 | 1 | 9 | 68.6 | 0.5 | 1.4 | 81.0 | 0.0 | 0.7 | described above, by contacting the heparinized human plasma solution with glass wool at a concentration of 5 g/L of plasma for about 15–18 hours at a temperature of about 2–8° C. The glass wool was subsequently removed from the solution by filtering.

Glycine was added to the heparinized human, bovine and activated plasma solutions to 1% by weight, and the plasma solutions were then combined in various relative amounts, as summarized in Table 3A, as 1 ml mini-pilots.

Each of the control compositions were subsequently evaluated using prothrombin time (PT) and activated partial thromboplastin time (APTT) assays as-prepared without lyophilization and reconstitution. Data was collected on an Amelung AMAX CS-190 coagulation analyzer using a PT reagent with an ISI value of 2.0 (Sigma ThromboMAX™) and APTT reagent that is moderately sensitive to heparin and to lupus anticoagulant (Sigma APTT-FSL). Both mechanical and optical determinations were made. The results are shown in Table 3A for both PT assays and APTT assays.

Pilot No. 3, comprising about 96% normal human plasma, about 3% glass-wool activated plasma and about 1% bovine plasma, by volume, was within the pilot target values for mechanical PT (11.3–12.8 seconds) and mechanical APTT (21–30 seconds). A coagulation control having the same composition as Pilot No. 3 was subsequently prepared in bulk in a production-scale process (20 liters), with glycine added to the bulk compositions to 1%, by weight. The production-scale Level I control composition was evaluated as-prepared ("bulk") and after lyophilization and reconstitution ("finished"), with data collection as described above, but only with mechanical testing. The results, shown in Table 3B, demonstrate that the Control Level I pilot composition was scalable to commercial quantities without loss of stability. Moreover, the production-scale Level I controls were within the bulk target values for mechanical PT (11.1–12.8 seconds) and mechanical APTT (20–32 seconds). Additional production runs were done at volumes up to 40 liters with similar results (data not shown).

TABLE 3A

Control Level I Pilot Compositions
(PT and APTT Data)

| | Lot Description | | | AMAX Pilot Data | | | |
|---|---|---|---|---|---|---|---|
| | Normal | Activated | Normal | PT | | APTT | |
| Pilot No. | Human Plasma % | Human Plasma % | Bovine Plasma % | Mechanical secs | Optical secs | Mechanical secs | Optical secs |
| 1 | 100 | 0 | 0 | 12.6 | 11.3 | 26.0 | 22.9 |
| 2 | 99 | 0 | 1 | 12.5 | 11.3 | 26.4 | 23.0 |
| 3* | 96 | 3 | 1 | 11.7 | 10.7 | 26.3 | 22.9 |
| 4 | 94 | 5 | 1 | 11.7 | 10.4 | 26.4 | 23.2 |

*Pilot combination chosen for production-scale evaluation

TABLE 3B

Control Level I Production-Scale
(PT and APTT Data)
AMAX Data
(Mechanical)

| | PT (secs) | APTT (secs) |
|---|---|---|
| Pilot | 11.7 | 26.3 |
| Bulk | 12.0 | 27.0 |
| Finished | 12.2 | 27.2 |

Example 4

Preparation of Level II Coagulation Controls

In order to prepare Level II coagulation controls suitable to mimic the plasma of patients under mild anticoagulation therapy, nine Level II control compositions, designated as Pilot No.'s 1–9, were prepared and evaluated as follows.

Heparinized normal human plasma solution, heparinized normal bovine plasma solution and heparinized factor-deficient human plasma solution, each comprising 0.05 U/ml heparin and 50 mM HEPES, were prepared as described in Example 3.

The heparinized normal human, normal bovine and factor-deficient human plasma solutions were then combined in various relative amounts, as summarized in Table 4A, as 1 ml mini-pilots.

Each of the control compositions were subsequently evaluated using prothrombin time (PT) and activated partial thromboplastin time (APTT) assays as-prepared, without lyophilization and reconstitution. Data was collected on an Amelung AMAX CS-190 coagulation analyzer using a PT reagent with an ISI value of 2.0 (Sigma ThromboMAX™) and APTT reagent that is moderately sensitive to heparin and to lupus anticoagulant (Sigma APTT-FSL). Only mechanical determinations were made. The results are shown in Table 4A for both PT assays and APTT assays.

Pilot No. 8, comprising about 77% factor-deficient human plasma, 19% normal human plasma, and about 4% bovine plasma, by volume, was within the pilot target values for mechanical PT (18–21 seconds) and mechanical APTT (51–55 seconds). A coagulation control having the same composition as Pilot No. 8, but with glycine added to 1%, by weight, was subsequently prepared in bulk in a production-scale process (20 liters). The production-scale Level II control composition was evaluated as-prepared ("bulk") and after lyophilization and reconstitution ("finished"), with data collection as described above. The results, shown in Table 4B, demonstrate that the Control Level II pilot composition was scalable to commercial quantities without loss of stability. Moreover, the production-scale Level II controls were within the bulk target values for mechanical PT (17–22 seconds) and mechanical APTT (50–57 seconds). Additional production runs at up to 40 liter were also carried out with similar results (data not shown).

TABLE 4A

Control Level II Pilot Compositions
(PT and APTT Data)

| | Lot Description | | | AMAX Pilot Data (Mechanical) | |
|---|---|---|---|---|---|
| Pilot No. | Factor-Deficient Human Plasma % | Normal Bovine Plasma % | Normal Human Plasma % | PT secs | APTT secs |
| 1 | 79 | 4 | 17 | 18.1 | 58.0 |
| 2 | 78 | 4 | 18 | 17.8 | 56.5 |
| 3 | 80 | 4 | 16 | 18.4 | 58.4 |
| 4 | 79 | 2 | 19 | 17.9 | 59.4 |
| 6 | 80 | 2 | 18 | 18.2 | 61.3 |
| 7 | 77 | 3 | 20 | 16.7 | 53.8 |
| 8* | 77 | 4 | 19 | 17.2 | 54.1 |
| 9 | 77.5 | 4 | 18.5 | 17.4 | 55.7 |

*Pilot combination chosen for production-scale evaluation

TABLE 4B

Control Level II Production-Scale
(PT and APTT Data)
AMAX Data
(Mechanical)

| | PT (secs) | APTT (secs) |
|---|---|---|
| Pilot | 17.2 | 54.1 |
| Bulk | 18.1 | 53.4 |
| Finished | 17.8 | 56.4 |

Example 5
Preparation of Level III Coagulation Controls

In order to prepare Level III coagulation controls suitable to mimic the plasma of patients under high anticoagulation therapy, eleven Level III control compositions, designated as Pilot No.'s 1–11, were prepared and evaluated as follows.

Heparinized normal human plasma solution, heparinized normal bovine plasma solution and heparinized factor-deficient human plasma solution, each comprising 0.05 U/ml heparin and 50 mM HEPES, were prepared as described in Example 3.

The heparinized normal human, normal bovine and factor-deficient human plasma solutions were then combined in various relative amounts, as summarized in Table 5A, as 1 ml minipilots.

Each of the control compositions were subsequently evaluated using prothrombin time (PT) and activated partial thromboplastin time (APTT) assays as-prepared, without lyophilization and reconstitution. Data was collected on an Amelung AMAX CS-190 coagulation analyzer using a PT reagent with an ISI value of 2.0 (Sigma ThromboMAX™) and APTT reagent that is moderately sensitive to heparin and to lupus anticoagulant (Sigma APTT-FSL). Only mechanical determinations were made. The results are shown in Table 5A for both PT assays and APTT assays.

Pilot No. 11, comprising about 90% factor-deficient human plasma, 6% normal human plasma, and about 4% bovine plasma, by volume, was within the pilot target values for mechanical PT (25–31 seconds) and mechanical APTT (71–79 seconds). A coagulation control having the same composition as Pilot No. 11, but with glycine added to 1%, by weight, was subsequently prepared in bulk in a production-scale process (10 liters). The production-scale Level III control composition was evaluated as-prepared ("bulk") and after lyophilization and reconstitution ("finished"), with data collection as described above. The results, shown in Table 5B, demonstrate that the Control Level III pilot composition was scalable to commercial quantities without loss of stability. Moreover, the production-scale Level III controls were within the bulk target values for mechanical PT (25–31 seconds) and mechanical APTT (71–80 seconds). Additional production runs were carried out at up to 40 l, with similar results (data not shown).

TABLE 5A

Control Level III Pilot Compositions
(PT and APTT Data)

| | Lot Description | | | AMAX Pilot Data (Mechanical) | |
|---|---|---|---|---|---|
| Pilot No. | Factor-Deficient Human Plasma % | Normal Bovine Plasma % | Normal Human Plasma % | PT secs | APTT secs |
| 1 | 89 | 2 | 9 | 24.5 | 74.7 |
| 2 | 90 | 2 | 8 | 25.8 | 78.0 |
| 3 | 91 | 2 | 7 | 27.2 | 81.7 |
| 4 | 92 | 2 | 6 | 29.4 | 88.2 |
| 5 | 93 | 2 | 5 | 32.4 | 94.0 |
| 6 | 94 | 2 | 4 | 35.3 | 105.6 |
| 7 | 95 | 2 | 3 | 41.6 | 121.1 |
| 8 | 89 | 3 | 8 | 24.4 | 75.1 |
| 9 | 90 | 3 | 7 | 26.9 | 79.5 |
| 10 | 91 | 4 | 5 | 28.9 | 81.9 |
| 11* | 90 | 4 | 6 | 27.5 | 77.9 |

*Pilot combination chosen for production-scale evaluation

TABLE 5B

Control Level III Production-Scale
(PT and APTT Data)
AMAX Data
(Mechanical)

| | PT (secs) | APTT (secs) |
|---|---|---|
| Pilot | 27.5 | 77.9 |
| Bulk | 29.1 | 75.3 |
| Finished | 27.8 | 80.8 |

Example 6
Stability Studies of Production-Scale Level I, II and III Coagulation Controls The Level I, Level II and Level III coagulation controls prepared in production-scale runs as described in Example 3, Example 4 and Example 5, respectively, were evaluated for reconstituted stability.

Each of the control compositions were evaluated using prothrombin time (PT) and activated partial thromboplastin time (APTT) assays. The assays were carried out on controls immediately after being reconstituted with water to the same volume as the volume at which the vials were filled before lyophilization, and also at times of 8 hours, 24 hours and 48 hours after being reconstituted. The reconstituted solutions were stored at about 2–8° C. Data was collected on an Amelung AMAX CS-190 coagulation analyzer using a PT reagent with an ISI value of 2.0 (Sigma ThromboMAX™) and APTT reagent that is moderately sensitive to heparin and to lupus anticoagulant (Sigma APTT-FSL). Both optical and mechanical determinations were made.

Figure 1B:
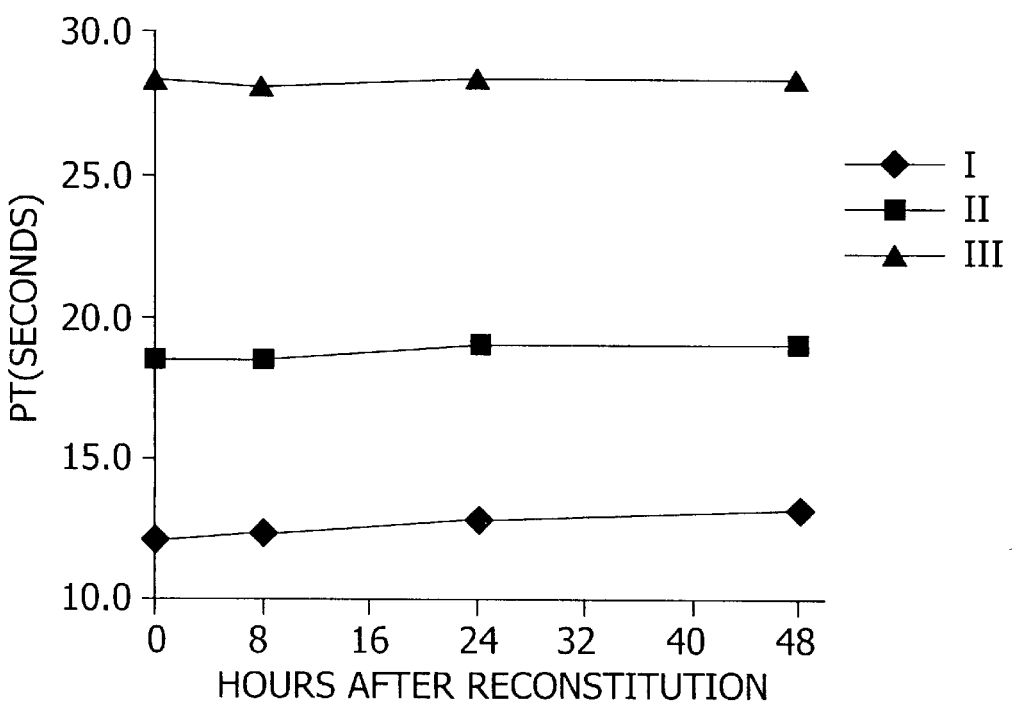

The results are shown in Table 6A for the PT assays and in Table 6B for the APTT assays. The data in these tables are also presented in FIGS. 1A and 1B for optical PT and mechanical PT, respectively, and in FIGS. 2A and 2B for optical APTT and mechanical APTT, respectively. These data demonstrate that the Level I, II and III controls prepared according to the protocols described and claimed herein have superior stability—even up to 48 hours after being reconstituted.

TABLE 6A

Stability of Level I, II, and III Controls (PT Data)

| Hours after Reconstitution | PT (seconds) AMAX CS-190 Optical | | | PT (seconds) AMAX CS-190 Mechanical | | |
|---|---|---|---|---|---|---|
| | I | II | III | I | II | III |
| 0 | 11.0 | 17.3 | 27.2 | 12.1 | 18.6 | 28.2 |
| 8 | 11.2 | 17.3 | 26.5 | 12.3 | 18.5 | 28.1 |
| 24 | 11.4 | 17.2 | 26.3 | 12.7 | 18.9 | 28.3 |
| 48 | 11.9 | 17.5 | 26.5 | 13.1 | 19.0 | 28.3 |

TABLE 6B

Stability of Level I, II, and III Controls (APTT Data)

| Hours after Reconstitution | APTT (seconds) AMAX CS-190 Optical | | | APTT (seconds) AMAX CS-190 Mechanical | | |
|---|---|---|---|---|---|---|
| | I | II | III | I | II | III |
| 0 | 32.0 | 52.7 | 71.1 | 35.8 | 58.2 | 77.9 |
| 8 | 32.5 | 53.2 | 71.5 | 36.1 | 58.2 | 77.7 |
| 24 | 33.7 | 53.9 | 71.7 | 37.5 | 59.5 | 78.1 |
| 48 | 34.5 | 54.1 | 71.7 | 38.6 | 59.6 | 78.2 |

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

I claim:

1. A coagulation control suitable for evaluating prothrombin time (PT) or activated partial thromboplastin time (APTT) assays, the coagulation control comprising
    an abnormal plasma, and
    a heparin derivative having activity for enhancing the activity of antithrombin III (ATIII) or of heparin co-factor II (HCII) against thrombin or against a clotting factor selected from the group consisting of factors IXa, Xa and XIa.

2. A coagulation control suitable for evaluating prothrombin time (PT) or activated partial thromboplastin time (APTT) assays, the coagulation control comprising
    an abnormal plasma, and
    a heparin analog having activity for enhancing the activity of antithrombin III (ATIII) or of heparin co-factor II (HCII) against thrombin or against a clotting factor selected from the group consisting of factors IXa, Xa and XIa.

3. A coagulation control suitable for evaluating prothrombin time (PT) or activated partial thromboplastin time (APTT) assays, the coagulation control comprising
    an abnormal plasma which is a factor-deficient plasma deficient in one or more clotting factors selected from the group consisting of factors II, VII, IX and X, and
    an anticoagulant having activity for enhancing the activity of antithrombin III (ATIII) or of heparin co-factor II (HCII) against thrombin or against a clotting factor selected from the group consisting of factors IXa, Xa and XIa.

4. A coagulation control suitable for evaluating prothrombin time (PT) or activated partial thromboplastin time (APTT) assays, the coagulation control comprising
    an abnormal plasma derivative, and
    an anticoagulant having activity for enhancing the activity of antithrombin III (ATIII) or of heparin co-factor II (HCII) against thrombin or against a clotting factor selected from the group consisting of factors IXa, Xa and XIa.

5. A coagulation control suitable for evaluating prothrombin time (PT) or activated partial thromboplastin time (APTT) assays, the coagulation control comprising a solution comprising
    a primate plasma,
    a non-primate mammalian plasma, and
    an anticoagulant having activity for enhancing the activity of antithrombin III (ATIII) or of heparin co-factor II (HCII) against thrombin or against a clotting factor selected from the group consisting of factors IXa, Xa and XIa, the concentration of anticoagulant ranging from about 0.01 U/ml to about 0.15 U/ml, where U is heparin-equivalent units.

6. The coagulation control of claim 5 wherein the concentration of anticoagulant ranges from about 0.01 U/ml to about 0.1 U/ml.

7. The coagulation control of claim 5 wherein the concentration of anticoagulant ranges from about 0.03 U/ml to about 0.07 U/ml.

8. The coagulation control of claim 5 wherein the concentration of anticoagulant is about 0.05 U/ml.

9. The coagulation control of claim 5 wherein the anticoagulant is a glycosaminoglycan.

10. The coagulation control of claim 5 wherein the anticoagulant is heparin.

11. The coagulation control of claim 5 wherein the anticoagulant is a heparin derivative.

12. The coagulation control of claim 5 wherein the anticoagulant is a heparin analog.

13. The coagulation control of claim 5 wherein the primate plasma or the non-primate mammalian plasma is whole plasma.

14. The coagulation control of claim 5 wherein the primate plasma or the non-primate mammalian plasma is a plasma derivative.

15. The coagulation control of claim 5 wherein the primate plasma is normal primate plasma.

16. The coagulation control of claim 5 wherein the primate plasma is a factor-deficient primate plasma deficient in one or more clotting factors selected from the group consisting of factors II, VII, IX and X.

17. The coagulation control of claim 5 wherein the primate plasma is an activated primate plasma.

18. The coagulation control of claim 5 wherein the primate plasma is human plasma.

19. The coagulation control of claim 5 wherein the non-primate mammalian plasma is bovine plasma.

20. The coagulation control of claim 5 wherein the non-primate mammalian plasma is bovine plasma present in the solution in an amount ranging from about 0.5% to about 12% by volume.

21. The coagulation control of claim 5 wherein
the primate plasma is human plasma present in the solution in an amount ranging from about 78% to about 99.5% by volume, and
the non-primate mammalian plasma is bovine plasma present in the solution in an amount ranging from about 0.5% to about 12% by volume.

22. The coagulation control of claim 5 wherein the solution is reconstituted from a lyophilized composition.

23. The coagulation control of claim 5 wherein the primate plasma is normal human plasma, the non-primate mammalian plasma is bovine plasma, and the anticoagulant is heparin or a heparin derivative.

24. The coagulation control of claim 23 wherein
the normal human plasma is present in the solution in an amount ranging from about 88% to about 98% by volume,
the bovine plasma is present in the solution in an amount ranging from about 2% to about 4% by volume, and
the concentration of heparin or a heparin derivative ranges from about 0.01 U/ml to about 0.1 U/ml.

25. The coagulation control of claim 23 wherein the concentration of heparin or heparin derivative ranges from about 0.01 U/ml to about 0.1 U/ml and the coagulation control further comprises an activated plasma.

26. The coagulation control of claim 25 wherein the coagulation control has a prothrombin time ranging from about 9 seconds to about 14 seconds as determined using a thromboplastin reagent having an International Sensitivity Index (ISI) of about 2.

27. The coagulation control of claim 25 wherein
the normal human plasma is present in the solution in an amount ranging from about 78% to about 99.5% by volume,
the bovine plasma is present in the solution in an amount ranging from about 0.5% to about 12% by volume, and
the activated plasma is activated human plasma present in the solution in an amount of not more than about 7% by volume.

28. The coagulation control of claim 25 wherein
the solution further comprises a buffer,
the normal human plasma is present in the solution in an amount ranging from about 88% to about 95% by volume,
the bovine plasma is present in the solution in an amount ranging from about 2% to about 4% by volume, and
the activated plasma is a glass-wool-activated human plasma present in the solution in an amount ranging from about 3% to about 5% by volume.

29. The coagulation control of claim 23 wherein the concentration of heparin or heparin derivative ranges from about 0.01 U/ml to about 0.1 U/ml, and the solution further comprises a factor-deficient human plasma deficient in one or more clotting factors selected from the group consisting of factors II, VII, IX and X.

30. The coagulation control of claim 29 wherein the coagulation control has a prothrombin time ranging from about 15 seconds to about 25 seconds as determined using a thromboplastin reagent having an International Sensitivity Index (ISI) of about 2.

31. The coagulation control of claim 29 wherein
the factor-deficient human plasma is present in the solution in an amount ranging from about 75% to about 85% by volume,
the bovine plasma is present in the solution in an amount ranging from about 0.5% to about 12% by volume, and
the normal human plasma is present in the solution in an amount ranging from about 0.5% to about 24.5% by volume.

32. The coagulation control of claim 29 wherein
the solution further comprises a buffer,
the factor-deficient human plasma is present in the solution in an amount ranging from about 78% to about 82% by volume,
the bovine plasma is present in the solution in an amount ranging from about 2% to about 4% by volume, and
the normal human plasma is present in the solution in an amount ranging from about 11% to about 20% by volume.

33. The coagulation control of claim 29 wherein the coagulation control has a prothrombin time ranging from about 25 seconds to about 33 seconds as determined using a thromboplastin reagent having an International Sensitivity Index (ISI) of about 2.

34. The coagulation control of claim 29 wherein
the factor-deficient human plasma is present in the solution in an amount ranging from about 85% to about 95% by volume,
the bovine plasma is present in the solution in an amount ranging from about 0.5% to about 12% by volume, and
the normal human plasma is present in the solution in an amount ranging from about 0.5% to about 14.5% by volume.

35. The coagulation control of claim 29 wherein
the solution further comprises a buffer,
the factor-deficient human plasma is present in the solution in an amount ranging from about 88% to about 92% by volume,
the bovine plasma is present in the solution in an amount ranging from about 2% to about 4% by volume, and
the normal human plasma is present in the solution in an amount ranging from about 1% to about 10% by volume.

36. A coagulation control suitable for evaluating prothrombin time (PT) or activated partial thromboplastin time (APTT) assays, the coagulation control comprising
primate plasma,
non-primate mammalian plasma, and
an anticoagulant having activity for enhancing the activity of antithrombin III (ATIII) or of heparin co-factor II (HCII) against thrombin or against a clotting factor selected from the group consisting of factors IXa, Xa and XIa, the concentration of anticoagulant ranging from about 0.1 U/g to about 1.8 U/g on a dry-weight basis where U is heparin-equivalent units.

37. The coagulation control of claim 36 wherein the concentration of anticoagulant ranges from about 0.3 U/g to about 1.2 U/g.

38. The coagulation control of claim 36 wherein the concentration of anticoagulant ranges from about 0.4 U/g to about 0.8 U/g.

39. The coagulation control of claim 36 wherein the concentration of anticoagulant is about 0.6 U/g.

40. A coagulation control suitable for evaluating prothrombin time (PT) or activated partial thromboplastin time (APTT) assays, the coagulation control comprising human plasma and non-primate mammalian plasma, the ratio of non-primate mammalian plasma to human plasma ranging from about 1:200 to about 1:5.

41. The coagulation control of claim 40 wherein the ratio of non-primate mammalian plasma to human plasma ranges from about 1:50 to about 1:20.

42. The coagulation control of claim 40 wherein the coagulation control is a solution.

43. The coagulation control of claim 40 wherein the coagulation control is a solution comprising the non-primate mammalian plasma in an amount ranging from about 0.5% to about 12% by volume.

44. The coagulation control of claim 40 wherein the coagulation control is a solution comprising the non-primate mammalian plasma in an amount ranging from about 2% to about 4% by volume.

45. The coagulation control of claim 40 wherein the human plasma or the non-primate mammalian plasma is whole plasma.

46. The coagulation control of claim 40 wherein the human plasma or the non-primate mammalian plasma is a plasma derivative.

47. The coagulation control of claim 40 wherein the human plasma is normal human plasma.

48. The coagulation control of claim 40 wherein the human plasma is a factor-deficient human plasma deficient in one or more clotting factors selected from the group consisting of factors II, VII, IX and X.

49. The coagulation control of claim 40 wherein the human plasma is an activated human plasma.

50. The coagulation control of claim 40 wherein the non-primate mammalian plasma is bovine plasma.

51. The coagulation control of claim 40 wherein the non-primate mammalian plasma is bovine plasma present in an amount ranging from about 0.5% to about 12% by volume.

52. The coagulation control of claim 40 wherein the non-primate mammalian plasma is bovine plasma present in an amount ranging from about 2% to about 4% by volume.

53. The coagulation control of claim 40 wherein
the human plasma is present in an amount ranging from about 78% to about 99.5% by volume, and
the non-primate mammalian plasma is bovine plasma present in an amount ranging from about 0.5% to about 12% by volume.

54. The coagulation control of claim 40 wherein the coagulation control is a lyophilized composition.

55. The coagulation control of claim 40 wherein the coagulation control is a solution reconstituted from a lyophilized composition.

56. A method for preparing a coagulation control suitable for evaluating prothrombin time (PT) or activated partial thromboplastin time (APTT) assays, the method comprising
combining primate plasma, non-primate mammalian plasma and an anticoagulant having activity for enhancing the activity of antithrombin III (ATIII) or of heparin co-factor II (HCII) against thrombin or against a clotting factor selected from the group consisting of factors IXa, Xa and XIa to form a control solution having an anticoagulant concentration ranging from about 0.01 U/ml to about 0.15 U/ml, where U is heparin-equivalent units.

57. A coagulation control prepared according to the method of claim 56.

58. The method of claim 56 for preparing a coagulation control suitable for evaluating prothrombin time (PT) and activated partial thromboplastin time (APTT) assays, the method comprising
combining human plasma and non-primate mammalian plasma to form a control solution comprising non-primate mammalian plasma in an amount ranging from about 0.5% to about 12% by volume.

59. A coagulation control prepared according to the method of claim 58.

60. A coagulation control suitable for evaluating prothrombin time (PT) or activated partial thromboplastin time (APTT) assays, the coagulation control comprising a solution comprising
an abnormal plasma, and
an anticoagulant having activity for enhancing the activity of antithrombin III (ATIII) or of heparin co-factor II (HCII) against thrombin or against a clotting factor selected from the group consisting of factors IXa, Xa and XIa, the concentration of anticoagulant ranging from about 0.01 U/ml to about 0.15 U/ml, where U is heparin-equivalent units.

61. The coagulation control of claim 60 wherein the concentration of anticoagulant ranges from about 0.01 U/ml to about 0.1 U/ml.

62. The coagulation control of claim 60 wherein the concentration of anticoagulant ranges from about 0.03 U/ml to about 0.07 U/ml.

63. The coagulation control of claim 60 wherein the concentration of anticoagulant is about 0.05 U/ml.

64. The coagulation control of claim 60 wherein the anticoagulant is a glycosaminoglycan.

65. The coagulation control of claim 60 wherein the anticoagulant is heparin.

66. The coagulation control of claim 60 wherein the anticoagulant is a heparin derivative.

67. The coagulation control of claim 60 wherein the anticoagulant is a heparin analog.

68. The coagulation control of claim 60 wherein the abnormal plasma is a factor-deficient plasma deficient in one of more clotting factors selected from the group consisting of factors II, VII, IX and X.

69. The coagulation control of claim 60 wherein the abnormal plasma is an activated plasma.

70. The coagulation control of claim 60 wherein the abnormal plasma is an abnormal whole plasma.

71. The coagulation control of claim 60 wherein the abnormal plasma is an abnormal plasma derivative.

* * * * *

UNITED STATES PATENT AND TRADEMARK OFFICE
CERTIFICATE OF CORRECTION

PATENT NO. : 6,194,394 B1  
DATED : February 27, 2001  
INVENTOR(S) : Pamela L. Hawkins Page 1 of 1

Figure 2A:
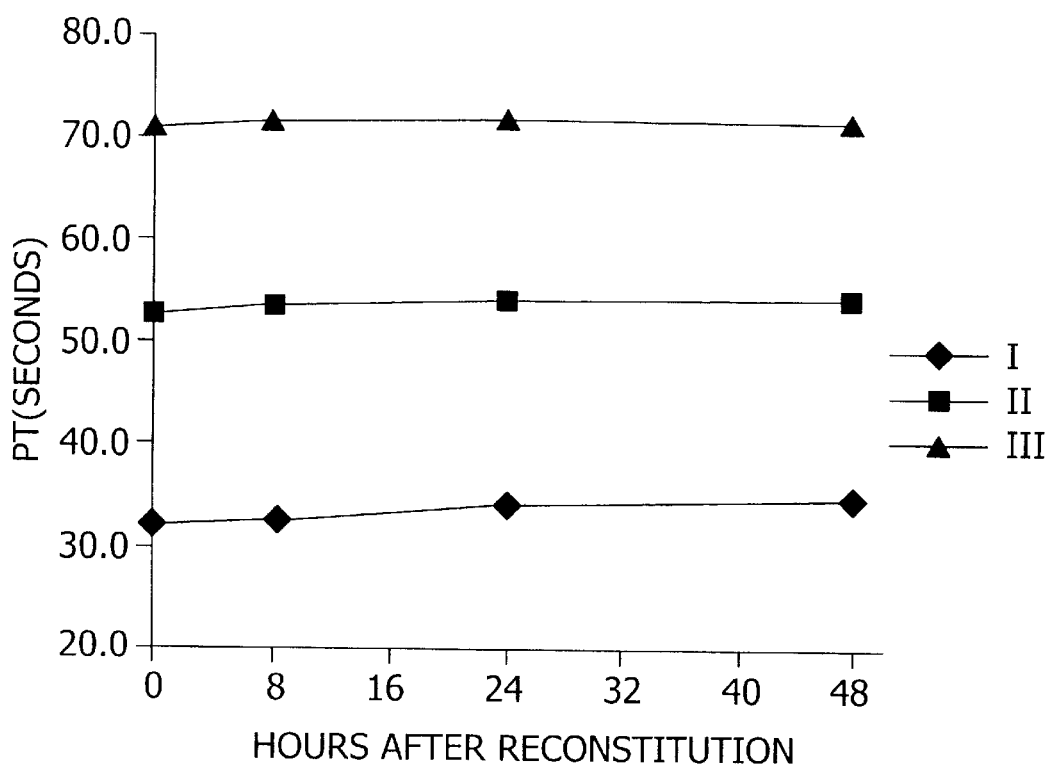
FIG. 2A and FIG. 2B are graphical representations of activated partial thromboplastin time (APTT) stability data for Level I, Level II and Level III coagulation controls prepared according to the methods of the present invention, and stored, after being reconstituted, at 2–8° C. Data was collected on an Amelung AMAX CS-190 coagulation analyzer using an APTT reagent that is moderately sensitive to heparin and to lupus anticoagulant (Sigma APTT-FSL). Both optical (FIG. 2A) and mechanical (FIG. 2B) determinations were made.
Figure 2B:
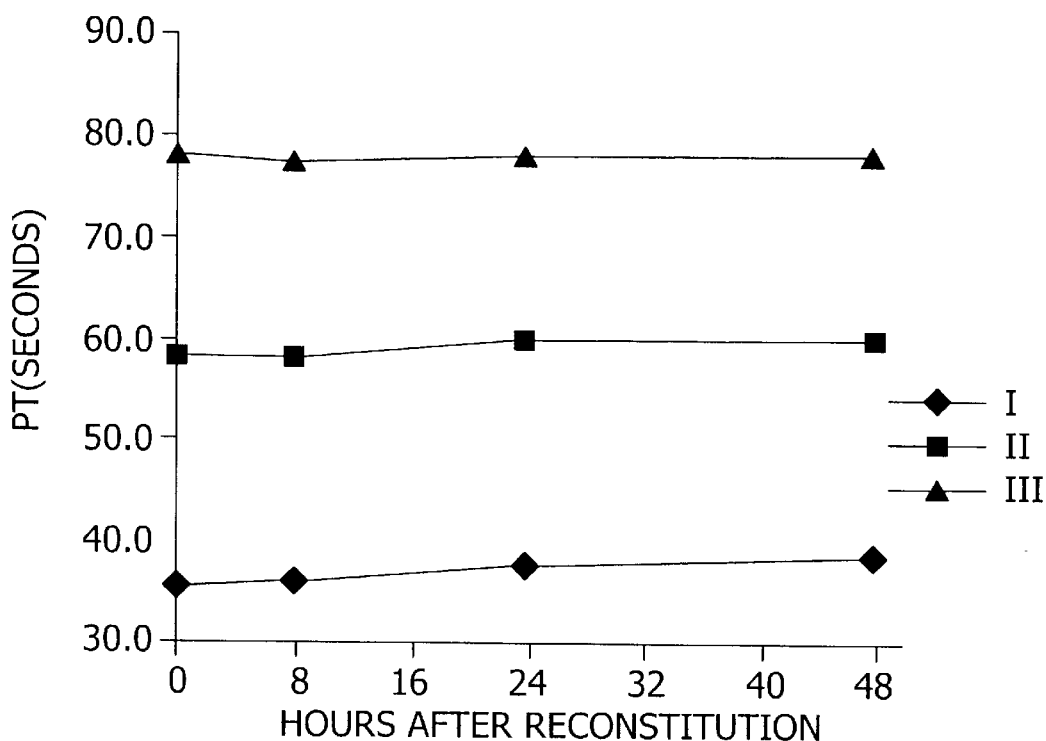

It is certified that error appears in the above-identified patent and that said Letters Patent is hereby corrected as shown below:

<u>Drawing Sheet 2 of 2,</u>
Fig. 2A, y-axis reference, "PT(SECONDS)" should read -- APTT(SECONDS) --.
Fig. 2B, y-axis reference, "PT(SECONDS)" should read -- APTT(SECONDS) --.

<u>Column 30, claim 68,</u>
Lines 47 and 48, "in one of more" should read -- in one or more --.

Signed and Sealed this

Fifth Day of February, 2002

*Attest:*

JAMES E. ROGAN
*Attesting Officer*   *Director of the United States Patent and Trademark Office*